United States Patent [19]

Brown et al.

[11] Patent Number: 5,008,220
[45] Date of Patent: Apr. 16, 1991

[54] BIOLOGICAL SUPPORT

[75] Inventors: Alan J. Brown, Milledgeville, Ga.; Roger James, Cornwall; Nigel P. Glasson, Dorset, both of United Kingdom

[73] Assignee: ECC International Limited, United Kingdom

[21] Appl. No.: 311,221

[22] Filed: Feb. 15, 1989

[30] Foreign Application Priority Data

Feb. 15, 1988 [GB] United Kingdom ................. 8803413

[51] Int. Cl.$^5$ .............................................. C04B 38/06
[52] U.S. Cl. ....................................... 501/81; 501/80; 501/129; 264/44
[58] Field of Search .................... 501/80, 128, 129, 81; 264/42, 48, 49, 44

[56] References Cited

U.S. PATENT DOCUMENTS

| | | | |
|---|---|---|---|
| 3,021,195 | 2/1962 | Podschus et al. | 23/110 |
| 3,526,602 | 9/1970 | Kobayashi et al. | 252/443 |
| 3,855,172 | 12/1974 | Iler et al. | 260/39 |
| 3,943,072 | 3/1976 | Thomson et al. | 252/455 |
| 4,601,997 | 7/1986 | Speronello | 501/263 |
| 4,628,042 | 12/1986 | Speronello | 501/263 |
| 4,937,209 | 6/1990 | Jones et al. | 501/80 |
| 4,937,210 | 6/1990 | Jones et al. | 501/80 |

FOREIGN PATENT DOCUMENTS

| | | |
|---|---|---|
| 56785/86 | 11/1986 | Australia . |
| 130734 | 1/1985 | European Pat. Off. . |
| 0185551 | 6/1986 | European Pat. Off. . |
| 187007 | 9/1986 | European Pat. Off. . |
| 793393 | 4/1958 | United Kingdom . |
| 1555230 | 11/1979 | United Kingdom . |
| 1948889 | 2/2964 | United Kingdom . |

OTHER PUBLICATIONS

Brindley et al, J. American Ceramic Soc. 42, No. 7, Jul., 1959, pp. 319-324.

Primary Examiner—Mark L. Bell
Assistant Examiner—Chris Gallo
Attorney, Agent, or Firm—Klauber & Jackson

[57] ABSTRACT

There is disclosed a porous inorganic material suitable for use as a support for immobilizing biological macromolecules and which comprises a 3-dimensional network of defect aluminium-silicon spinel, said network defining an interconnecting array of pores predominantly in the size range of from 100 to 1000 Å.

A process for preparing the porous inorganic material is also disclosed.

20 Claims, 1 Drawing Sheet

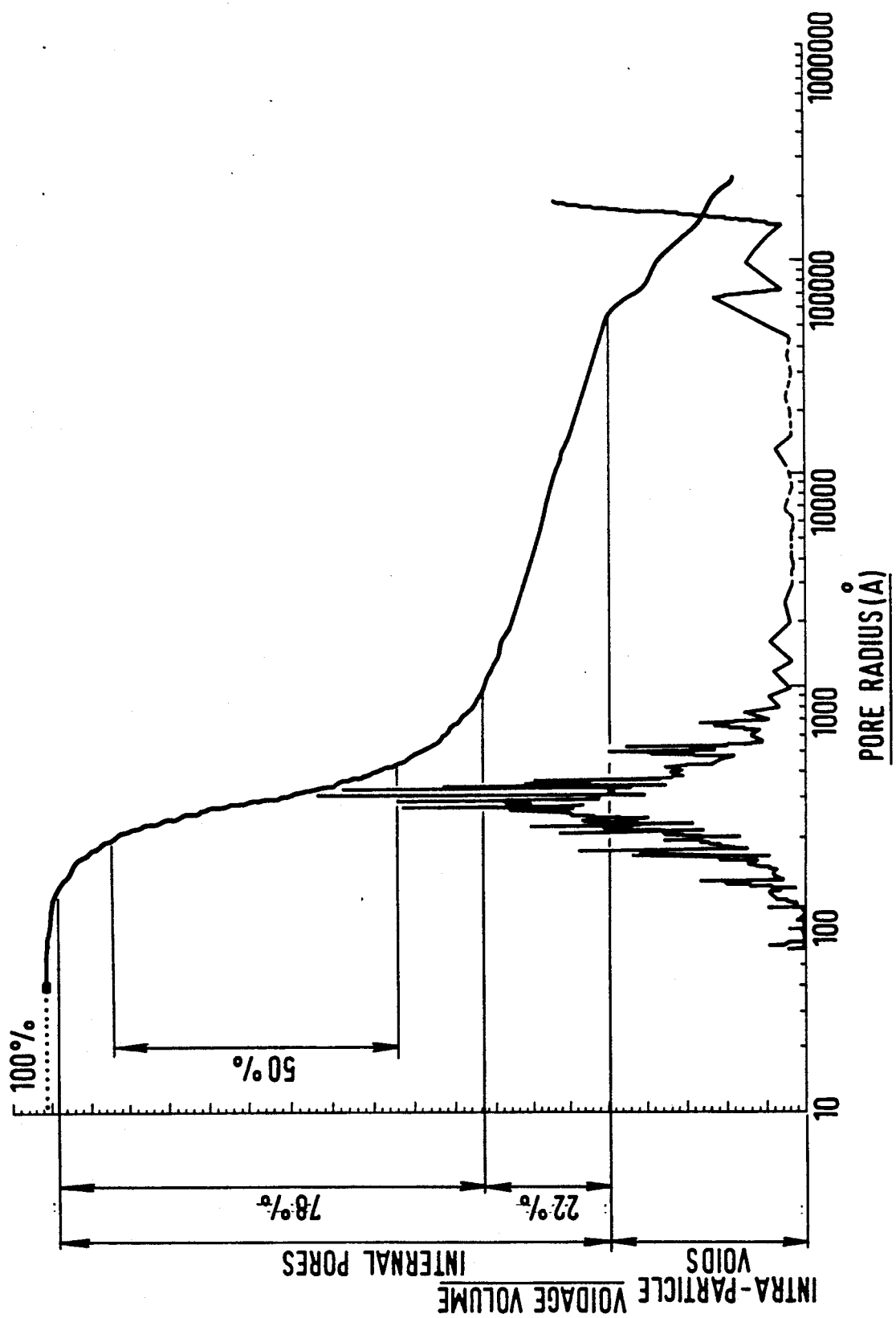

BIOLOGICAL SUPPORT

This invention relates to a porous inorganic material which is suitable for retaining and protecting biological macromolecules such as enzymes and proteins.

BACKGROUND OF THE INVENTION

It is often required, when performing a biochemical reaction, to pass a liquid or a gaseous medium containing reagents or nutrients though a chamber in which a reagent or a catalyst in the form of biological macromolecules is substantially uniformly distributed in fixed, but spaced-apart, locations. For this purpose it is necessary to support the biological macromolecules in a material which mobilizes and protects the biological macromolecules whilst permitting free passage of the medium through the chamber.

Porous inorganic materials in the form of beads, granules or particles of more irregular shape have been used to support biological macromolecules. If the inorganic materials are to be used to pack a large column in which a biochemical reaction is to be carried out on a commercial scale, it is necessary for the material to be sufficiently porous to provide cavities in which the biological macromolecules can be immobilised, while retaining sufficient mechanical strength to resist the crushing effect of the weight of the packing material in the column.

THE PRIOR ART

GB-2153807 relates to a porous particulate aluminosilicate material which is prepared by calcining at 1000° C. to 1800° C. an aluminosilicate material having an $SiO_2:Al_2O_3$ molar ratio of at least 0.75:1 to form mullite crystals and silica; and leaching away the silica to leave an interconnecting pore network.

EP-0130734 and EP-0187007 are concerned with the production of porous mullite to be used as a support for precious metal catalysts.

Whilst there are references in the art to the production of porous materials by firing a clay in which there is distributed a combustible material, the ultimate product invariably has relatively large pores in the micron and millimetre ranges. Such references of which we are aware are British Patent Specifications Nos. 1274735, 1233220, 769225, 638299, 393246 and 266165.

Whilst ball clays may be used in the production of ceramic articles, such articles are produced by firing the clay at a temperature in excess of 1200° C. thereby producing a product consisting essentially of mullite, and not a defect spinel structure.

THE INVENTION 7

According to a first aspect of the invention, there is provided a process for preparing a porous inorganic material suitable for use as a support for retaining biological macromolecules, which process comprises: (a) calcining a kaolinitic clay in which there is distributed from 5% to 25%, by weight of the clay, of a carbonaceous material having a particle size no greater than about 1000 Å, at a temperature and for a time such that a substantial portion of the kaolinitic clay is converted to porous, defect aluminium-silicon spinel without appreciable formation of mullite, the spinel having an interconnecting array of pores predominantly in the size range of from about 100 to about 1000 Å; and (b) isolating said porous defect aluminium-silicon spinel without further calcination.

According to a second aspect of the invention, there is provided a porous inorganic material comprising a 3-dimensional network of defect aluminium-silicon spinel, said network defining an interconnecting array of pores predominantly in the size range of from about 100 to about 1000 Å.

According to a third aspect of the present invention, there is provided a method of retaining biological macromolecules within a porous inorganic material having a 3-dimensional network of defect aluminium-silicon spinel which defines an interconnecting array of pores predominantly in the size range of from about 100 to about 1000 Å, which method comprises the step of introducing the biological macromolecules into said interconnecting array of pores and causing or permitting said macromolecules to distribute within said pores.

DETAILED DESCRIPTION

The porous inorganic material of the present invention may be used, for example, for retaining and protecting, or immobilising, biological macromolecules in a chamber in which a biochemical reaction is carried out.

The biological macromolecules, retained within the porous inorganic material may then be used to perform biological reactions. For example, in the rapidly expanding biotechnology field, it is becoming possible to isolate, in significant quantities, specific enzymes as well as specific (or monoclonal) antibodies. The biological support of the present invention is believed to provide a particularly effective means by which these biological macromolecules may be supported.

The porous inorganic material may be itself supported within a chamber, for example packed within a column.

When kaolinitic clay is heated to a temperature above about 550° C. an endothermic reaction takes place and chemically bound water is released to give the product which is generally know as metakaolin. If, however, the temperature is increased to about 925° C. an exothermic reaction begins to become evident and the material which is formed is often referred to as "kaolin which has undergone the characteristic exothermic reaction". The material formed by calcining a kaolinitic clay at a temperature in the range from about 925° to about 1050° C. is also referred to as a defect aluminium-silicon spinel or as gamma alumina. A further name which is sometimes used is "incipient mullite" but it is to be distinguished from mullite proper because its crystals are very much smaller than those of mullite. In this specification, the term "defect aluminium-silicon spinel," or simply "defect spinel", is used throughout. On further heating of the defect spinel material to a temperature above about 1050° C., mullite proper is formed. The process of the present invention is normally conducted at a temperature in excess of about 925° C. and below about 1050° C.

The natural kaolinitic clay preferably contains from 10% to 20% by weight of the very finely divided carbonaceous material. The carbonaceous material may be added artificially in the form of, for example, carbon black. However, it is more convenient to use a kaolinitic clay which contains the desired amount of carbonaceous material in its natural state, for example a lignitic ball clay.

As the kaolinitic clay is calcined, the carbonaceous material is burnt and vapourised to leave the desired pore structure. To produce a fine pore structure, the carbonaceous material should be finely divided into particles which have a maximum size no greater than 1000 Å. Moreover, the particles should be intimately mixed with the kaolinitic clay as this gives the desired narrow distribution of relatively fine pores. A natural lignitic ball clay generally possesses carbonaceous lignite in the required state of division and intimate mixture with the kaolinite. Preferably a natural ball clay having very fine particle size is used. Such a clay tends to include lignitic particles which are even finer than the clay particles.

Biological catalysts of the globular protein or enzyme type generally have diameters in the range of from 10 to 50 Angstrom (Å). It has been found that if a porous inorganic material is to be able effectively to immobilise these catalyst macromolecules it should have pores predominantly in the size range of from 100 to 1000 Å (10 to 100 nanometres) and most preferably most of the pores should be in the size range 200 to 400 Å (20 to 40 nanometres).

Preferably, the kaolinitic clay should have a particle size distribution such that at least 75% by weight of the particles have an equivalent spherical diameter (e.s.d.) smaller than 2 micrometres and at least 65% by weight of the particles have an (e.s.d.) smaller than 1 micrometre. It has been found that, if a lignitic ball clay containing from 10% to 20% by weight of carbon and having a particle size distribution of the type specified above is calcined at a temperature in the range from 925° to 1050° C., the diameters of the pores formed by combustion of the carbonaceous material are concentrated in the relatively narrow size range of from 200 to 400 Å (20 to 40 nm) which has been found to be an ideal size range for immobilising proteins and enzymes. Typically, at least 65% by volume of the pores lie in the broad range of 100 to 1000 Å, whilst at least 40% lie in the narrow 200 to 400 Å range. It is believed that the heat of combustion of the carbonaceous material combined with the heat evolved by the exothermic reaction undergone by the kaolinitic clay fuses the primary kaolinite particles together to form hard but porous granules. It is not necessary to leach the granules with alkali to remove any silica which may be present.

Preferably, the kaolinitic clay is formed before calcination into shaped bodies having diameters in the range of from 0.2 mm to 3.5 mm. The water content of the kaolinitic clay is advantageously adjusted before formation of the shaped bodies to lie in the range from about 1% to about 50% by weight, and preferably in the range from about 28% to about 35% by weight.

The kaolinitic clay which is thus in a plastic state is then advantageously granulated by means of a peg- or pan-type granulator, or extruded to form spaghetti-like material which is then chopped to yield particles in the desired size range. If shaped bodies having diameters in the desired size range are calcined under the conditions specified above the product consists of hard porous particles which have size, shape and mechanical properties suitable for use as a packing material in a column for performing a biochemical reaction.

The natural kaolinitic clay is preferably exposed to a temperature in the required range for a time which will be sufficient to convert substantially all the kaolin or metakaolin to the defect spinel form but not sufficient to produce an appreciable quantity of mullite. For example, if the calcining temperature is 925° C. the kaolinitic clay should be exposed to this temperature for about 2 hours. However, if the temperature is 1050° C. the time for which the clay is exposed to this temperature should not exceed about 1 hour.

The calcining operation may be performed as a batch process, in which case the temperature of the kaolinitic clay may be brought slowly up to the desired level over a period of several hours, provided that the clay is not allowed to remain at a temperature in the range of from 925° to 1050° C. for longer than about 1 to 2 hours.

Alternatively, and more preferably, the calcination may be performed continuously using, for example, a rotary or fluidised bed calciner. The atmosphere during the calcining operation should preferably be of an oxidising nature to aid combustion of the carbonaceous material which is mixed with the kaolinitic clay.

The porous inorganic material may be used as a biological catalyst support either in the condition in which it is produced by the calcining operation, or after coating with a suitable reacting layer for the purposes, in particular, of affinity chromatography, ion exchange or certain biochemical separations such as the size exclusion separation of biological macromolecules. Examples of materials which can be coated on to the porous inorganic material to form reactive layers include polymeric organic acids, polymeric quaternary ammonium compounds or polyacidic organic bases such as polyethyleneimines, which will form bonds directly with the surface of the defect spinel. These materials possess both hydrophilic and hydrophobic groups and anion or cation exchange properties, which are useful in biological applications such as treating or separating proteins. Other materials which can be coated directly on to the defect spinel include thermoplastic materials such as polystyrene and polysaccharides. An example of a substituted polysaccharide material which has been found to form a useful reactive layer is "DEAE Dextran" which is a dextran substituted with pendant diethylamine ethyl groups: this provides an hydrophilic organic layer with anion exchange properties.

The surface of the porous inorganic material may be rendered hydrophobic, and be given an overall positive charge, by applying a coating of a quaternary ammonium compound which has at least one hydrocarbon radical with from 10 to 24 carbon atoms such as dimethyl di (hydrogenated tallow) ammonium chloride or polydimethyldiallyl ammonium chloride. Alternatively, the particulate porous material may be given an overall negative charge by applying a coating of, for example, a polymer or a co-polymer of a sulphonated acrylic acid or acrylamide.

Some materials can only be used to form reactive layers after the defect spinel has first been coated with a bonding agent. Suitable bonding agents are substituted silanes, especially those comprising at least one hydroxy, hydroxyalkyl or alkoxy group for bonding with hydroxyl groups on the surface of the defect spinel and at least one aminoalkyl, diazo or haloalkyl group for bonding with the material of the desired layer. An example of a suitable substituted silane is 3-aminopropyltriethoxysilane. Reactive layer materials which will form bonds with the substituted silane include nucleic acid bases, such as adenine which is very useful for the concentration and separation of nucleic acids and polysuccinimide which is very suitable for affinity chromatography and for immobilising enzymes.

Reference will now be made to the following Examples.

EXAMPLE 1

A raw lignitic ball clay having a particle size distribution such that 80% by weight consisted of particles having an equivalent spherical diameter smaller than 2 micrometres, 70% by weight consisted of particles having an equivalent spherical diameter smaller than 1 micrometre and 55% by weight consisted of particles having an equivalent spherical diameter smaller than 0.5 micrometre, and containing 15% by weight of carbon, predominantly in the form of lignite, was shredded and partially dried to a water content of 28% by weight. The partially dried, shredded clay was then fed to a pan granulator which was provided with a high speed rotating agitator and with paddle blades which were rotated at a slower speed in a direction opposite to the direction of rotation of the pan. A fine water spray moistened the clay during the granulation. The product consisted of substantially spherical granules of size predominantly in the range of from 0.2 mm to 3.5 mm and a water content of 31% by weight. The granules were dried in an oven to a water content of 18.7% by weight and the partially dried granules were separated by sieving into particle size fractions of from 0.5 to 0.8 mm and from 0.8 to 1.6 mm respectively. Each size fraction was then calcined to a porous defect spinel material on a batch basis in a kiln, the temperature of which was increased steadily from 20° C. to 1000° C. over a period of 14.5 hours, after which it was held at 1000° C. for 1 hour before the kiln and its contents were allowed to cool. The specific surface area of a sample from each case was found to be approximately 20 $m^2g^{-1}$.

The pore size distribution of the 0.8 to 1.6 mm size fraction was investigated by a conventional mercury intrusion porosimetry technique using a scanning mercury porosimeter. The curve which was obtained is shown in the FIGURE. As shown in the FIGURE, the voidage at the large end of the spectrum must be ignored as intra-particle voids. Of the remaining voidage, approximately 78% by volume is in the size range 100 to 1000 Å whilst about 50% is in the size range 200 to 400 Å.

EXAMPLE 2

The crushing strength of samples taken from the two size fractions of porous defect spinel material produced in Example 1 was determined by resting large steel weights in the range of from 0.5 to 20 kg on single granules and observing the greatest weight which the granule could support without being crushed. For each size fraction the crushing strength was found to be about 3 kg.

EXAMPLE 3

The degree of adsorption of protein to a porous inorganic material in accordance with the invention was investigated by adding 1 g of the porous material to 15 ml of an aqueous solution containing 100 ppm of myoglobin, and subjecting the mixture to mild agitation in the form of a gentle tumbling action for 18 hours to allow equilibrium to be reached. The mixture was then allowed to stand for 5 hours and centrifuged for 5 minutes at 3000 rpm to separate the porous inorganic material from the solution of unabsorbed protein. The protein content of the initial solution and of the solution of the unabsorbed protein separated by the centrifuge was determined by ultraviolet spectrophotometry and the difference between the two measurements gave a measure of the quantity of myoglobin in milligrams which was adsorbed by 1 gram of the porous material. The specific surface area of the porous material was also determined by the BET nitrogen adsorption method.

The porous inorganic materials investigated in the above manner were:

A. the 0.5 mm to 0.8 mm size fraction of defect spinel material produced in Example 1;
B. a commercially available controlled pore glass enzyme support-material; and
C. a commercially available cross-linked organic matrix enzyme-support-material.

The results obtained are set forth in Table I below:

TABLE 1

| Material | Specific surface are ($m^2 \cdot g^{-1}$) | Weight of protein adsorbed ($mg \cdot g^{-1}$) |
|---|---|---|
| A | 20 | 1.5 |
| B | 30 | 0.37 |
| C | 2.1 | 1.1 |

As can be seen from the above results the porous defect spinel material adsorbed a larger weight of protein per gram than either of the commercially available materials even through its specific surface area was less than that of material B.

We claim:

1. A process for preparing a porous inorganic material suitable for use as a support for immobilising biological macromolecules, which process comprises: (a) calcining a kaolinitic clay in which there is distributed from 5% to 25%, by weight of the clay, of a carbonaceous material having a particle size no greater than about 1000 Å, at a temperature and for a time such that a substantial portion of the kaolinitic clay is converted to porous, defect aluminium-silicon spinel without appreciable formation of mullite, the spinel having an interconnecting array of pores predominantly in the size range of from about 100 to about 1000 Å; and (b) recovering said porous defect aluminium-silicon spinel without further calcination.

2. A process according to claim 1 in which the calcination temperature is no greater than about 1050° C.

3. A process according to claim 1, wherein the calcination temperature is no less than about 950° C.

4. A process according to claim 1, wherein the carbonaceous material is present in an amount in the range of from 10% to 20% by weight, based on the weight of the clay.

5. A process according to claim 3, wherein the kaolinitic clay and the carbonaceous material are exposed to the temperature in excess of 950° C. for a time not exceeding about two hours.

6. A process according to claim 1, wherein at least 65% by volume of the pores in the material lie in the size range of from about 100 to about 1000 Å.

7. A process according to claim 1, wherein at least 40% by volume of the pores in the material lie in the size range of from about 200 to about 400 Å.

8. A process according to claim 1, wherein, prior to calcination, the water content of the kaolinitic clay in which the carbonaceous material is distributed is adjusted to lie in the range of from about 1% to about 50% by weight.

9. A process according to claim 8, wherein the water content is adjusted to lie in the range of from about 20% to about 35% by weight.

10. A process according to claim 1, wherein, prior to calcination, the kaolinitic clay is formed into shaped bodies having diameters in the range of from 0.2 mm to 3.5 mm.

11. A process according to claim 1, wherein the kaolinitic clay used is a lignitic ball clay.

12. A porous inorganic material comprising a 3-dimensional network of defect aluminium-silicon spinel, said network defining an interconnecting array of pores predominantly in the size range of from 100 to 1000 Å.

13. A porous inorganic material according to claim 12 wherein at least 65% by volume of the pores in the material lie in the size range of from about 100 to 1000 Å.

14. A porous inorganic material according to claim 13, wherein at least 40% by volume of the pores of the material lie in the size range of from 200 to 400 Å.

15. A porous inorganic material according to claim 12, in which the 3-dimensional solid network further includes free silica in addition to the defect spinel.

16. A porous material according to claims 12, comprising shaped bodies having diameters in the range of from 0.2 millimetres to 3.5 millimetres.

17. A porous inorganic material according to claim 12, in which the 3-dimensional solid network is coated with a reactive layer.

18. A packed column in which the packed material is discrete particles of a porous inorganic material comprising a 3-dimensional network of defect aluminum-silicon spinel, said network defining an interconnecting array of pores predominantly in the size range of from 100 to 1000 Angstroms.

19. A packed column according to claim 18 wherein said pores contain biological macromolecules.

20. A packed column according to claim 18 wherein said discrete particles are spheres.

* * * * *